United States Patent [19]
Van Der Puy

[11] Patent Number: 6,111,139
[45] Date of Patent: Aug. 29, 2000

[54] PROCESS FOR THE PREPARATION OF TRIFLUOROPROPANAL

[76] Inventor: Michael Van Der Puy, 3 Exeter Rd., Amherst, N.Y. 14221

[21] Appl. No.: 09/433,474

[22] Filed: Nov. 4, 1999

[51] Int. Cl.$^7$ .................................................. C07C 249/08
[52] U.S. Cl. ......................... 564/253; 564/259; 568/487; 568/489
[58] Field of Search ..................... 568/488, 487, 568/490, 495, 485; 564/253, 259

[56] References Cited

U.S. PATENT DOCUMENTS

| | | | |
|---|---|---|---|
| 2,739,987 | 3/1956 | Ruh | 260/614 |
| 2,883,429 | 4/1959 | Haszeldine | 568/604 |
| 4,622,427 | 11/1986 | Baasner et al. | 564/261 |
| 5,434,175 | 7/1995 | Babin et al. | 514/378 |
| 5,777,184 | 7/1998 | Van Der Puy et al. | 570/135 |

OTHER PUBLICATIONS

CA:102:6263 abs of Bull Chem Soc Jpn by Tanaka et al 57(8) pp. 2184–2187, 1984.

"Advanced Organic Chemistry:Reactions, Mechanisms and Structure" textbook by J. March, McGraw–Hill Book C., New York p. 306, 1968.

Haszeldine, R.N.; "Reactions of Fluorocarbon Radicals. Part VII. Addition to Trifluoromethyl–substituted Acetylenes". J.Chem Soc. No. 669, p. 3490–98, 1952.

Hong, Feng, et al "A novel and convenient synthesis of (Z)–3,3,3–trifluoropropenyl alkyl ethers and $CF_3$ substituted propyl acetals as verasatile $CF_3$–containing building blocks" J.Chem.Soc.Chem.Commun. 1996; p. 57–8.

Pazenok, et al "β–Perfluoroalkylvinyl Alkyl Ethers"; J. Org. Chem. USSR, Engl. Transl. 25 (1989) p. 1238–41.

*Primary Examiner*—Jean F. Vollano
*Attorney, Agent, or Firm*—Colleen Szuch; Marie Collazo

[57] ABSTRACT

A compound having the formula 3,3,3-trifluoropropanal oxime, and an improved process for forming 3,3,3-trifluoropropanal and its oxime. The process for producing 3,3,3-trifluoropropanal involves reacting an alkali or alkaline earth metal salt of an alcohol, which alcohol has the formula ROH, where R is a $C_1$–$C_4$ alkyl, with $CF_3CH=CHCl$ under conditions sufficient to yield a product mixture comprising at least one of $CH_3CH=CHOR$ and $CF_3CH_2CH(OR)_2$; and then reacting the product mixture of with a $C_3$–$C_{16}$ alkanoic acid, and heating under conditions sufficient to form 3,3,3-trifluoropropanal. The oxime is prepared by reacting hydroxylamine with 3,3,3-trifluoropropanal under conditions sufficient to produce 3,3,3-trifluoropropanal oxime.

26 Claims, No Drawings

PROCESS FOR THE PREPARATION OF TRIFLUOROPROPANAL

BACKGROUND OF THE INVENTION

This invention relates to the preparation of 3,3,3-trifluoropropanal, $CF_3CH_2CHO$, and its oxime. More particularly, it relates to an improved process for forming 3,3,3-trifluoropropanal and 3,3,3-trifluoropropanal oxime.

Fluorinated compounds, particularly trifluoromethylated compounds, are known for enhancing the effectiveness of agricultural products and pharmaceuticals. Examples of extensively used trifluoromethyl compounds include trifluoroethanol, trifluoroacetic acid, trifluoroacetaldehyde, and trifluoroacetyl chloride. Higher molecular weight homologs are generally not commercially available in bulk quantities since preparations which are convenient, economical, and environmentally acceptable, have yet to be developed.

Several methods have been developed for the preparation of trifluoropropanal. However, reduction of the corresponding acid chloride or oxidation of the corresponding alcohol suffers from the lack of availability of the precursor, and variable yields. Specific problems associated with these approaches can be found in U.S. Pat. No. 5,777,184. Better methods use $CF_3CH=CHOR$, where R is usually methyl or ethyl, as a key intermediate. These enol ethers can be made by the addition of methanol or ethanol to trifluoropropyne. For example, the addition of NaOMe to trifluoropropyne gives Z—$CF_3CH=CHOMe$ (R. N. Hazeldine, *J. Chem. Soc.*, 1952, 3490). However, trifluoropropyne is not readily available. The methyl enol ether can be prepared by reacting 2-bromo-3,3,3-trifluoropropene with NaOH in aqueous methanol. (F. Hong and C-M. Hu, *J. Chem. Soc., Chem. Comm.* 1996, 57).

Furthermore, 1-chloro-3,3,3-trifluoropropene ($CF_3CH=CHCl$) has also been used as a starting material for the preparation of trifluoropropanal. U.S. Pat. No. 5,777,184 outlines a method where the chloride is converted into the corresponding acetate in a palladium-catalyzed process, which is subsequently hydrolyzed to the aldehyde. The preferred method for the preparation of $CF_3CH=CHCl$ is given in Example 1 in U.S. Pat. No. 5,777,184 which is incorporated herein by reference. This process suffers from relatively few catalyst turnovers before deactivation occurs. In another process, described in U.S. Pat. No. 2,739,987, the chloride is converted into E—$CF_3CH=CHOMe$ with KOH in methanol. This process not only gives a different isomer of $CF_3CH=CHOMe$ than that obtained from either trifluoropropyne or $CF_3CBr=CH_2$, but the yield of the enol ether is substantially lower.

Even if $CF_3CH=CHOMe$ were available, its conversion to trifluoropropanal is still problematic. The enol ether has been known to behave very unusually in that reduction using freshly prepared Raney-nickel gives trifluoropropanal (R. N. Hazeldine, *J Chem. Soc.*, 1952, 3490). Although the yield was high, a large weight of catalyst is used compared to the organic starting material. Furthermore, the aldehyde is isolated only as a derivative. Aqueous HI can be used to convert $CF_3CH=CHOMe$ to the aldehyde (R. P. Ruh., U.S. Pat. No. 2,739,987, 1965). Although the yield is good, aqueous HI is expensive. Pazenok et al. (J. Org. Chem. USSR, Engl. Transl. 25 (1989) 1238) hydrolyzed the enol ether with dilute mineral acid (10% HCl), a standard method for this transformation. However, they found the stoichiometry to be

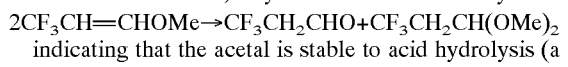

indicating that the acetal is stable to acid hydrolysis (a standard method for converting acetals to aldehydes). The yield of aldehyde, based on this stoichiometry was only 44%, while the yield of acetal was 76%. Consequently, the prior art methods for making the aldehyde from $CF_3CH=CHCl$ have a very poor overall yield.

It would be desirable to provide a process for making 3,3,3-trifluoropropanal which is easier, less expensive, and has a higher yield that other known methods. This invention provides an improved process for producing 3,3,3-trifluoropropanal, as well as a process for making a previously unknown compound, 3,3,3-trifluoropropanal oxime.

DESCRIPTION OF THE INVENTION

The invention provides a process for producing 3,3,3-trifluoropropanal which comprises:

a) reacting an alkali or alkaline earth metal salt of an alcohol, of the formula ROH, where R is a $C_1$–$C_4$ alkyl, with $CF_3CH=CHCl$ under conditions sufficient to yield a product mixture comprising at least one of $CH_3CH=CHOR$ and $CF_3CH_2CH(OR)_2$; and b) reacting the product mixture of step (a) with a $C_3$–$C_{16}$ alkanoic acid under conditions sufficient to form 3,3,3-trifluoropropanal.

The invention further provides the compound, 3,3,3-trifluoropropanal oxime, and a process for producing 3,3,3-trifluoropropanal oxime which comprises reacting hydroxylamine with 3,3,3-trifluoropropanal under conditions sufficient to produce 3,3,3-trifluoropropanal oxime.

The invention still further provides a process for producing 3,3,3-trifluoropropanal oxime which comprises:

a) reacting a hydroxylamine salt with sufficient base to form hydroxylamine; and b) reacting the hydroxylamine with 3,3,3-trifluoropropanal under conditions sufficient to produce 3,3,3-trifluoropropanal oxime.

The invention still further provides a process for producing 3,3,3-trifluoropropanal oxime which comprises:

a) reacting an alkali or alkaline earth metal salt of an alcohol, which alcohol has the formula ROH, where R is a $C_1$–$C_4$ alkyl, with $CF_3CH=CHCl$ under conditions sufficient to yield a product mixture comprising at least one of $CH_3CH=CHOR$ and $CF_3CH_2CH(OR)_2$; and b) reacting the product mixture of step (a) with a $C_3$–$C_8$ alkanoic acid under conditions sufficient to form 3,3,3-trifluoropropanal; and then c) reacting the 3,3,3-trifluoropropanal with hydroxylamine under conditions sufficient to produce 3,3,3-trifluoropropanal oxime.

This invention provides a process for the production of 3,3,3-trifluoropropanal. In a first step (a) of this process, an alkali or alkaline earth metal salt of an alcohol having the formula ROH (where R is $C_1$–$C_4$ alkyl) is reacted with $CF_3CH=CHCl$ to form a product mixture. The $C_1$–$C_4$ alkyl group can be any isomer thereof and can optionally be substituted with any moiety which does not have a detrimental effect on the reaction. Optional substituents include $C_1$–$C_4$ alkoxy groups. The reaction is preferably conducted in a suitable solvent such as the base alcohol of the salt or DMSO. A preferred solvent is methanol or ethanol. In a second step (b), the product mixture of step (a) is reacted with a $C_3$–$C_{16}$ alkanoic acid, preferably a $C_6$–$C_8$ alkanoic acid, and heated under conditions sufficient to form 3,3,3-trifluoropropanal. The alkanoic acid may optionally be substituted with any moiety which does not have a detrimental effect on the reaction. Suitable substituents may be alkyl groups, aryl groups, alkoxy groups and halogens. Optionally, the additional step of separating 3,3,3-trifluoropropanal may be taken. This step is preferably conducted the end of step (b) where the end product of that step is isolated as a separate liquid phase by distillation. Suitable alkali or alkaline earth metal salts nonexclusively include sodium methoxide, potassium tert-butoxide, sodium ethoxide, and lithium sec-butoxide. Preferred salts are sodium methoxide and sodium ethoxide.

Step (a) is preferably conducted under substantially anhydrous conditions. This step is also preferably conducted at a temperature of from about 25° C. to about 200° C., more preferably at a temperature of from about 50° C. to about 100° C. This heating is preferably conducted for a time sufficient to form a product comprising at least one of $CH_3CH=CHOR$ and $CF_3CH_2CH(OR)_2$ where R is $C_1-C_4$ alkyl. This amount of time preferably ranges from about 1 hour to about 50 hours, more preferably from about 1 hour to about 25 hours, and most preferably from about 1 hour to about 20 hours. The mole ratio of alkali or alkaline earth metal salt to $CF_3CH=CHCl$ preferably ranges from about 1 to about 2 moles of salt per mole of $CF_3CH=CHCl$, more preferably from about 1.0 to about 1.5 and most preferably from about 1.0 to about 1.25. The reaction yields a product mixture comprising at least one of $CH_3CH=CHOR$ and $CF_3CH_2CH(OR)_2$.

In step (b), the product of step (a) is reacted with a $C_3-C_8$ alkanoic acid under heating conditions sufficient to form 3,3,3-trifluoropropanal. The alkanoic acid of step (b) preferably has at least 2 more carbon atoms than the alcohol salt used in step (a). Suitable alkanoic acids are preferably $C_3-C_{16}$ alkanoic acids, more preferably $C_3-C_8$ alkanoic acids, and most preferably $C_6-C_8$ alkanoic acids. The alkanoic acids with 6 to 8 carbons are most preferred because they have ideal physical properties for the process, are inexpensive, and are readily available in bulk quantities. The preferred alkanoic acids are hexanoic acid, heptanoic acid, and octanoic acid.

In a preferred embodiment of this invention, the molar amount of alkanoic acid in step (b) is at least equal to the molar amount of OR groups in the product mixture. More preferably, the molar amount of alkanoic acid in step (b) is from about 1 to about 3 times the molar amount of OR groups in the product mixture. Most preferably, the molar amount of alkanoic acid in step (b) is from about 1.2 to about 1.7 times the molar amount of OR groups in the product mixture.

Step (b) is preferably conducted by heating the product mixture in presence of a strong acid catalyst. This heating can be conducted by any conventional means. It is preferred that the heating is conducted at a temperature of from about 25° C. to about 150° C., more preferably from about 40° C. to about 130° C., and most preferably from about 50° C. to about 120° C. This heating is preferably conducted for a time sufficient to convert the product mixture of step (a) into trifluoropropanal. This amount of time preferably ranges from about 0.25 hours to about 15 hours, more preferably from about 0.5 hours to about 5 hours, and most preferably from about 1 hour to about 3 hours.

Strong acids may be employed as catalysts in this step, typically in the amount of 0.1–10 mole percent based on the product of step (a). Strong acids include those which have a Pka of about 1 or less. Nonexclusive examples of suitable strong acid catalysts include sulfuric acid, p-toluenesulfonic acid, methanesulfonic acid, and trifluoroacetic acid. Most preferred are sulfuric acid and methanesulfonic acid.

Yields of 3,3,3-trifluoropropanal from this process, starting from $CF_3CH=CHCl$, are in the 70–80% range.

A second process of this invention provides for the production of 3,3,3-trifluoropropanal oxime. Oximes of aldehydes are useful intermediates for the preparation of amines via reduction and the preparation of nitriles via dehydration. 3,3,3-Trifluoropropanal oxime is produced by reacting hydroxylamine with 3,3,3-trifluoropropanal under conditions sufficient to produce 3,3,3-trifluoropropanal oxime. 3,3,3-Trifluoropropanal oxime may be produced by reacting a hydroxylamine salt with sufficient base to form hydroxylamine, and then reacting the hydroxylamine with 3,3,3-trifluoropropanal under conditions sufficient to produce 3,3,3-trifluoropropanal oxime.

According to the invention, sufficient base means that amount of a base which sufficiently reacts with a hydroxylamine salt to form hydroxylamine. The amount of base may vary depending on which base and which hydroxylamine salt is used. The pKb of hydroxylamine is 8. Therefore bases should preferably have a pKb of about 8 or higher to generate free hydroxylamine. However, an equilibrium concentration is also effective, therefore even bases weaker than hydroxylamine will often suffice, i.e. those having a pKb of about 6 or higher.

Suitable bases nonexclusively include amines, salts of alkanoic acids, and hydroxides. Preferred hydroxides include sodium hydroxide, potassium hydroxide and ammonium hydroxide. Suitable hydroxylamine salts nonexclusively include hydroxylamine sulfate and hydroxylamine hydrochloride. The hydroxylamine salt may be reacted with the base at a temperature of from about 0° C. to about 50° C., for from about 1 minute to several hours to produce hydroxylamine. The preferred mole ratio of base to hydroxyamine may easily be determined by those skilled in the art, however, a mole ratio of about 1:1 is effective.

Then, hydroxylamine and 3,3,3-trifluoropropanal react to form 3,3,3-trifluoropropanal oxime. The hydroxylamine may be reacted with 3,3,3-trifluoropropanal at a temperature of about 0° C. to about 100° C., more preferably from about 0° C. to about 75° C., and most preferably from about 15° C. to about 35° C. for about 30 minutes to about 180 minutes to produce 3,3,3-trifluoropropanal oxime.

Trifluoropropanal is a useful intermediate, providing access to the corresponding alcohol, $CF_3CH_2CH_2OH$, via reduction and the heretofore unknown oxime. Yields of 3,3,3-trifluoropropanal oxime from this process are in the range of from about 60% to about 90%. Separation and recovery of the desired products may be by standard phase separation and distillation techniques. Useful methods include reaction in water, extraction with organic solvents and stripping with organic solvents to give the oxime. Suitable organic solvents are those with a boiling point of less than about 120° C.

The following non-limiting examples serve to illustrate the invention. It will be appreciated that variations in proportions and alternatives in the practice of the present invention will be apparent to those skilled in the art, and are within the scope of the invention.

EXAMPLE 1

3,3,3-Trifluoropropanal

A mixture of 85 mL of 25 wt % NaOMe in methanol, 15 mL methanol, and 46.2 g (0.354 mol) $CF_3CH=CHCl$ was heated in an autoclave at 70–80° C. for 19.5 hours. During the first hour an exotherm occurred wherein the temperature rose temporarily to 90–100° C. The pressure did not exceed 100 psig. The cooled reaction mixture was poured into 300 mL cold water. The lower layer was separated and washed once with 50 mL water. The crude product (39.8 g) is reacted in the next step without further treatment. By GC analysis, it consists of 84.3% $CF_3CH=CHOCH_3$ isomers (E/Z ratio about 10:1) and 9.4% $CF_3CH_2CH(OCH_3)_2$.

The crude material obtained above, 60 g hexanoic acid and 1.5 g methanesulfonic acid, were refluxed (bath temperature 110–120° C.) for 2 hours (analysis of the vapor phase shows the absence of the acetal). The condenser was then exchanged for a distillation column and the aldehyde (bp 55–60°, mainly 56–58° C.) was isolated by distillation. The yield of 99.4% pure aldehyde was 30.6 g (77% from $CF_3CH=CHCl$).

EXAMPLE 2
3,3,3-Trifluoropropanal oxime

Sodium hydroxide (10 g) was dissolved in 100 mL water. To this was added 17.4 grams of hydroxylamine hydrochloride, followed by the addition of 20 g of $CF_3CH_2CHO$ over 10 minutes, keeping the temperature at 20–25° C. with water bath cooling. Stirring was continued for an additional 2 hours before extracting the product with 2×50 mL methylene chloride. The combined extracts were dried ($Na_2SO_4$) and distilled to give 14.8 g (65% yield) of the desired oxime, bp 119–120° C., which solidified on standing at room temperature. Major isomer: $^1H$ NMR: d 3.3 (dq, J=11.0 and 5.2 Hz, 2H), 6.9 (t, J=5.2 Hz, 1 H), 9.3 (broad singlet, 1H); $^{19}F$ NMR: −65.3 (t, J=11 Hz). Minor isomer: $^1H$ NMR: d 3.1 (dq, J=10.2 and 6.2 Hz, 2 H), 7.4 (t, J=6.2 Hz, 1H), 8.8 (broad singlet, 1H); $^{19}F$ NMR: −65.4 (t, J=10.2 Hz) ppm. The mass spectra for these isomers were essentially identical.

EXAMPLE 3

Two hundred grams of a 21 wt % solution of sodium ethoxide in denatured ethyl alcohol (0.617 moles of NaOEt) and 80.9 g (0.62 mol) of $CF_3CH=CHCl$ are combined in an autoclave and heated to 80–100° C. for 24 hours. The contents are cooled and diluted with 750 mL of cold water. The lower product phase is separated and washed with 100 mL cold water. The crude $CF_3CH=CHOEt$ so obtained is added to 175 g (1 mol) of capric acid (decanoic acid) containing 0.5 g of sulfuric acid. The mixture is heated in an oil bath until analysis of the vapor at reflux indicates the absence of the acetals ($CF_3CH_2CH(OEt)_2$ or mixed acetals, e.g., $CF_3CH_2CH(OEt)OCH_3$ stemming from other alcohols used in the denaturing of ethanol (about 4 hours). The product $CF_3CH_2CHO$ is then distilled out.

What is claimed is:

1. The compound, 3,3,3-trifluoropropanal oxime.

2. A process for producing 3,3,3-trifluoropropanal which comprises:
    a) reacting an alkali or alkaline earth metal salt of an alcohol, of the formula ROH, where R is a $C_1$–$C_4$ alkyl, with $CF_3CH=CHCl$ under conditions sufficient to yield a product mixture comprising at least one of $CH_3CH=CHOR$ and $CF_3CH_2CH(OR)_2$; and
    b) reacting the product mixture of step (a) with a $C_3$–$C_{16}$ alkanoic acid under conditions sufficient to form 3,3,3-trifluoropropanal.

3. The process of claim 2 further comprising the subsequent step of separating 3,3,3-trifluoropropanal.

4. The process of claim 2 wherein the salt is sodium methoxide.

5. The process of claim 2 wherein the salt is sodium ethoxide.

6. The process of claim 2 wherein step (a) is conducted under substantially anhydrous conditions.

7. The process of claim 2 wherein step (a) is conducted at a temperature of from about 25° C. to about 200° C.

8. The process of claim 2 wherein the mole ratio of salt to $CF_3CH=CHCl$ ranges from about 1 to about 2 moles of salt per mole of $CF_3CH=CHCl$.

9. The process of claim 2 wherein the alkanoic acid of step (b) is a $C_6$–$C_8$ alkanoic acid.

10. The process of claim 2 wherein the molar amount of alkanoic acid in step (b) is at least equal to the molar amount of OR groups in the product mixture.

11. The process of claim 2 wherein the molar amount of alkanoic acid in step (b) is from about 1.2 to about 1.7 times the molar amount of OR groups in the product mixture.

12. The process of claim 2 wherein step (b) is conducted by heating in presence of a strong acid catalyst.

13. The process of claim 12 wherein the strong acid catalyst is sulfuric acid.

14. The process of claim 12 wherein the strong acid catalyst is methanesulfonic acid.

15. The process of claim 2 wherein step (b) is conducted by heating.

16. The process of claim 2 wherein step (b) is conducted at a temperature of from about 25° C. to about 150° C.

17. A process for producing 3,3,3-trifluoropropanal oxime which comprises reacting hydroxylamine with 3,3,3-trifluoropropanal under conditions sufficient to produce 3,3,3-trifluoropropanal oxime.

18. A process for producing 3,3,3-trifluoropropanal oxime which comprises:
    a) reacting a hydroxylamine salt with sufficient base to form hydroxylamine; and
    b) reacting the hydroxylamine with 3,3,3-trifluoropropanal under conditions sufficient to produce 3,3,3-trifluoropropanal oxime.

19. The process of claim 18 wherein the hydroxylamine salt is hydroxylamine sulfate.

20. The process of claim 18 wherein the hydroxylamine salt is hydroxylamine hydrochloride.

21. The process of claim 18 wherein the base is selected from the group consisting of amines, salts of alkanoic acids, hydroxides and mixtures thereof.

22. The process of claim 18 wherein the base comprises a hydroxide.

23. The process of claim 18 wherein the base is selected from the group consisting of sodium hydroxide, potassium hydroxide, ammonium hydroxide and mixtures thereof.

24. The process of claim 23 wherein the base comprises sodium hydroxide.

25. A process for producing 3,3,3-trifluoropropanal oxime which comprises:
    a) reacting an alkali or alkaline earth metal salt of an alcohol, which alcohol has the formula ROH, where R is a $C_1$–$C_4$ alkyl, with $CF_3CH=CHCl$ under conditions sufficient to yield a product mixture comprising at least one of $CH_3CH=CHOR$ and $CF_3CH_2CH(OR)_2$; and
    b) reacting the product mixture of step (a) with a $C_3$–$C_8$ alkanoic acid under conditions sufficient to form 3,3,3-trifluoropropanal; and then
    c) reacting the 3,3,3-trifluoropropanal with hydroxylamine under conditions sufficient to produce 3,3,3-trifluoropropanal oxime.

26. The process of claim 25 wherein the hydroxylamine is prepared by reacting a hydroxylamine salt with sufficient base to form hydroxylamine.

* * * * *

UNITED STATES PATENT AND TRADEMARK OFFICE
CERTIFICATE OF CORRECTION

PATENT NO. : 6,111,139
APPLICATION NO. : 09/433474
DATED : August 29, 2000
INVENTOR(S) : Michael Van Der Puy It is certified that error appears in the above-identified patent and that said Letters Patent is hereby corrected as shown below:

On the Title Page of the patent, insert:

--(73) Assignee: AlliedSignal Inc., Morristown, NJ--

Signed and Sealed this

Twenty-ninth Day of January, 2008

JON W. DUDAS
*Director of the United States Patent and Trademark Office*